US012392780B2

(12) United States Patent
Imai et al.

(10) Patent No.: US 12,392,780 B2
(45) Date of Patent: Aug. 19, 2025

(54) SUPPORT FOR FLUORESCENCE POLARIZATION IMMUNOASSAY, FLUORESCENCE POLARIZATION IMMUNOASSAY KIT AND FLUORESCENCE POLARIZATION IMMUNOASSAY

(71) Applicant: TIANMA JAPAN, LTD., Kanagawa (JP)

(72) Inventors: Ayuko Imai, Kanagawa (JP); Ken Sumiyoshi, Kanagawa (JP); Masanori Shirokawa, Kanagawa (JP)

(73) Assignee: TIANMA JAPAN, LTD., Kanagawa (JP)

( * ) Notice: Subject to any disclaimer, the term of this patent is extended or adjusted under 35 U.S.C. 154(b) by 222 days.

(21) Appl. No.: 17/647,052

(22) Filed: Jan. 5, 2022

(65) Prior Publication Data

US 2022/0221465 A1   Jul. 14, 2022

(30) Foreign Application Priority Data

Jan. 8, 2021   (JP) ................................ 2021-001841

(51) Int. Cl.
*G01N 33/58*   (2006.01)
*B01L 3/00*    (2006.01)
*G01N 21/64*   (2006.01)
*G01N 33/542*  (2006.01)

(52) U.S. Cl.
CPC .......... *G01N 33/582* (2013.01); *B01L 3/5027* (2013.01); *G01N 21/6428* (2013.01); *G01N 33/542* (2013.01); *B01L 2300/0829* (2013.01); *G01N 2021/6439* (2013.01)

(58) Field of Classification Search
CPC ............. G01N 33/582; G01N 21/6428; G01N 33/542; G01N 2021/6439; G01N 21/6452; G01N 21/6445; G01N 33/533; B01L 3/5027; B01L 2300/0829; B01L 2200/16; B01L 2300/0816; B01L 2300/0864; B01L 3/5088
See application file for complete search history.

(56) References Cited

U.S. PATENT DOCUMENTS

| | | | |
|---|---|---|---|
| 5,489,668 A | 2/1996 | Morrison et al. | |
| 6,429,026 B1 | 8/2002 | Pettersson et al. | |
| 2001/0051331 A1 | 12/2001 | Nakayama et al. | |
| 2003/0113713 A1 | 6/2003 | Glezer et al. | |
| 2005/0130226 A1* | 6/2005 | Ahn | G01N 33/54393 435/7.1 |
| 2007/0142568 A1 | 6/2007 | Kim et al. | |
| 2008/0273918 A1* | 11/2008 | Linder | G01N 33/5302 403/31 |
| 2010/0035245 A1 | 2/2010 | Stiene et al. | |
| 2014/0031249 A1* | 1/2014 | Lea | G01N 33/54306 506/9 |
| 2014/0273035 A1 | 9/2014 | Dowell et al. | |
| 2016/0017032 A1* | 1/2016 | Westerman | A61P 31/10 435/254.2 |

FOREIGN PATENT DOCUMENTS

| | | | | |
|---|---|---|---|---|
| JP | 03-103765 A | 4/1991 | | |
| JP | 4-253999 A | 9/1992 | | |
| JP | 06-130057 A | 5/1994 | | |
| JP | 2000-509486 A | 7/2000 | | |
| JP | 3255293 B2 | 2/2002 | | |
| JP | 2005-521032 A | 7/2005 | | |
| JP | 2009-506331 A | 2/2009 | | |
| JP | 2009-521686 A | 6/2009 | | |
| JP | 2016-510128 A | 4/2016 | | |
| KR | 20100010314 | * | 2/2010 | ............ G01N 33/48 |
| WO | WO 2011094577 | * | 8/2011 | ............... B01L 3/00 |

OTHER PUBLICATIONS

Wang et al., Development of a fluorescence polarization immunoassay for the detection of melamine in milk and milk powder. Anal Bioanal Chem (2011) 399:2275-2284. (Year: 2010).*
Choi et al., A droplet-based fluorescence polarization immunoassay (dFPIA) platform for rapid and quantitative analysis of biomarkers. Biosensors and Bioelectronics 67 (2015) 497-502 (Year: 2015).*
Berezin et al., Fluorescence Lifetime Measurements and Biological Imaging. Chem Rev. May 1, 20102; 110(5): 2641-2684 (Year: 2010).*
Office Action issued Jun. 25, 2024 in Japanese Application No. 2021-001841.
Li, et al., "Development of a Screening Fluorescence Polarization Immunoassay for the Simultaneous Detection of Fumonisins $B_1$ and $B_2$ in Maize", Journal of Agricultural and Food Chemistry, 2015, vol. 63, pp. 4940-4946 (7 pages).
Japanese Office Action dated Oct. 1, 2024, in Application No. 2021-001841.
Communication issued Jan. 21, 2025, in Japanese Application No. 2021-001841.
China Patent Office, Communication issued Jun. 6, 2025, by the Chinese Patent Office in copending Application No. 202210004789.2.

(Continued)

*Primary Examiner* — Ann Montgomery
(74) *Attorney, Agent, or Firm* — Sughrue Mion, PLLC

(57) ABSTRACT

Provided is a support for fluorescence polarization immunoassay of which reaction parts are loaded with an antibody and a fluorescent labeling substance. The plurality of reaction parts may be loaded with different concentrations of an antibody and a fluorescent labeling substance. Further, antibodies having different binding affinities for a target substance may be loaded. With such a support, fluorescence polarizations can be measured simply by adding a sample solution containing a target substance to the reaction parts, and a wide measurement range of the concentration the target substance can be secured.

19 Claims, 14 Drawing Sheets

(56) References Cited

OTHER PUBLICATIONS

Choi et al., "A droplet-based fluorescence polarization immunoassay (dFPIA) platform for rapid and quantitative analysis of biomarkers", Biosensors and Bioelectronics, 67, 2015, pp. 497-502.

* cited by examiner

SUPPORT FOR FLUORESCENCE POLARIZATION IMMUNOASSAY, FLUORESCENCE POLARIZATION IMMUNOASSAY KIT AND FLUORESCENCE POLARIZATION IMMUNOASSAY

CROSS-REFERENCE TO RELATED APPLICATION

This application claims the benefit of Japanese Patent Application No. 2021-1841, filed on Jan. 8, 2021, the entire disclosure of which is incorporated by reference herein.

FIELD

The present disclosure relates to a support for fluorescence polarization immunoassay loaded with an antibody and a fluorescent labeling substance, a fluorescence polarization immunoassay kit, and a fluorescence polarization immunoassay using the support for fluorescence polarization immunoassay.

BACKGROUND

Fluorescence polarization immunoassay is known as an immunity analysis method using fluorescence. Fluorescence polarization measured by the fluorescence polarization immunoassay is known to be proportional to the effective volume of a target substance. Unexamined Japanese Patent Application Publication No. H03-103765 describes a fluorescence polarization immunoassay which uses a reagent in which an antibody (or antigen) is immobilized on a substance having a larger molecular weight than the antibody, then, utilizes a significant change in the fluorescence polarization caused by a specific antigen-antibody reaction between this reagent and a fluorescently labeled antigen (or antibody).

There is also a method that measures a high molecular weight substance using a fluorescence polarization immunoassay (Japanese Patent No. 3255293). In an example of the method, pyrenebutanoic acid is used as a fluorescent dye, and a high density lipoprotein (HDL) calibration curve is created using an anti-HDL polyclonal antibody as an antibody that specifically binds to a target substance.

Such a fluorescence polarization immunoassay can be conducted using a multi-well plate containing a plurality of wells. Unexamined Japanese Patent Application Publication (Translation of PCT Application) No. 2005-521032 describes a module containing a plurality of assay domains, including a first assay domain with a first reagent and a second assay domain with a second reagent, in which the first assay domain is capable of producing luminescence at least 10 times brighter than the second assay domain with reduced interference between the luminescence emitted from the first assay domain and the luminescence emitted from the second assay domain. This is preferably performed in assay modules having an integrated electrode with a reader device configured to induce electrode-induced luminescence and to measure the induced luminescence (Summary). According to Unexamined Japanese Patent Application Publication (Translation of PCT Application) No. 2005-521032, a plurality of types of antibodies can be immobilized on one assay domain, and multiple test measurements can be performed using a module with a plurality of assay domains.

There is also a multi-well assay plate in which a plurality of wells contains: a binding surface to immobilize a capture reagent thereon; and a dry reagent that can be restored, and the dry reagent is arranged on the surface of the wells in a manner the dry reagent does not overlap the binding surface (Unexamined Japanese Patent Application Publication (Translation of PCT Application) No. 2009-521686). Since the dried reagent does not overlap the binding surface, even if an additional liquid reagent containing an assay control is dispensed and dried, the assay can be performed without making physical contact between the dried detection reagent and the dried assay control.

General assays require factors such as simple operation and low reagent amounts, in addition to high sensitivity and accuracy of the instruments and measurement systems used. The fluorescence polarization immunoassay is based on the principle of competitive binding immunoassay and uses two types of reagents: a fluorescence-labeled compound in which the same molecule as the molecule of a target substance is labeled with a fluorescent substance; and an antibody that specifically binds to the molecule of the target substance. When using a multi-well, a plurality of reagents is required to be added to each well, which makes the operation complicated. Therefore, development of a support for fluorescence polarization immunoassay and a fluorescence polarization immunoassay kit that are easy to operate is desired.

In a fluorescence polarization immunoassay, the concentration of a target compound can be quantified within a range within which the relationship between the fluorescence polarization and the concentration of the target substance has a certain correlation. If the concentration of a target substance in a sample solution falls outside this measurement range, the sample solution needs to be diluted and measured again. Therefore, when the width of the measurement range is wide, the dilution process of the sample solution can be omitted.

SUMMARY

As a result of detailed investigation of the fluorescence polarization immunoassay, the present disclosers completed the present disclosure by finding, for example, that, when the reaction parts of the support are, in advance, loaded with an antibody having an ability to bind to a target substance and a fluorescent labeling substance in which the target substance is labeled with a fluorescent dye, the fluorescence polarization immunoassay can be performed simply by adding a sample solution containing the target substance.

In other words, the present disclosure provides a support having reaction parts for a fluorescence polarization immunoassay of a target substance in a sample, in which the reaction parts are loaded with an antibody having a binding ability to the target substance and a fluorescent labeling substance in which the target substance is labeled with a fluorescent dye.

The present disclosure also provides the support for fluorescence polarization immunoassay, characterized in that the reaction parts are loaded with at least one of the fluorescent labeling substance or the antibody at different concentrations.

The present disclosure also provides the support for fluorescence polarization immunoassay, characterized in that the reaction parts are loaded with antibodies having different binding affinities for the target substance.

The present disclosure also provides the support for fluorescence polarization immunoassay, characterized in that the reaction parts are further loaded with a pH adjuster.

The present disclosure also provides the support for fluorescence polarization immunoassay, characterized in that the reaction parts are microfluidic channels.

The present disclosure also provides the support for fluorescence polarization immunoassay, characterized in that some of the reaction parts are connected through a communication path.

The present disclosure also provides the support for fluorescence polarization immunoassay, characterized in that the fluorescent dye is one or more selected from a group consisting of fluorescein, dansyl, pyrene, rhodamine, dialkylaminonaphthalene, dialkylaminonaphthalenesulfonyl, indolenine, and ruthenium.

The present disclosure also provides the support for fluorescence polarization immunoassay, characterized in that the fluorescent dye has a fluorescence life of 1 to 3,000 nanoseconds.

The present disclosure also provides a fluorescence polarization immunoassay kit that includes the support for fluorescence polarization immunoassay and a solvent for dissolving the target substance.

The present disclosure also provides a method of fluorescence polarization immunoassay, characterized by adding a sample solution containing the target substance to the reaction parts of the support for fluorescence polarization immunoassay, causing the target substance, the antibody, and the fluorescent labeling substance to react in the reaction parts, and performing a fluorescence polarization immunoassay of the reaction parts at a temperature of 4 to 40° C.

It is to be understood that both the foregoing general description and the following detailed description are exemplary and explanatory and are not restrictive of this disclosure.

BRIEF DESCRIPTION OF THE DRAWINGS

A more complete understanding of this application can be obtained when the following detailed description is considered in conjunction with the following drawings, in which.

DETAILED DESCRIPTION

Figure 1:
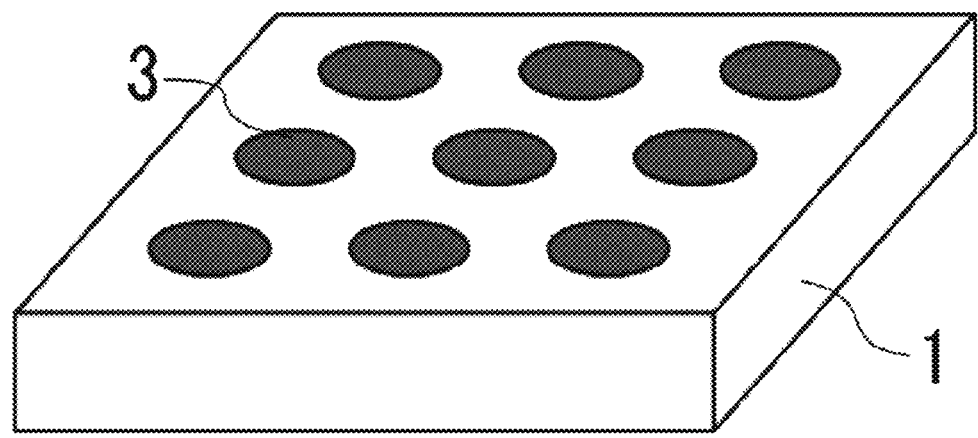
FIG. 1 is a diagram of a support for fluorescence polarization immunoassay with circular reaction parts formed in three vertical and horizontal rows.

The present disclosure provides a support having reaction parts for a fluorescence polarization immunoassay of a target substance in a sample, in which the reaction parts are loaded with an antibody having a binding ability to the target substance and a fluorescent labeling substance in which the target substance is labeled with a fluorescent dye. Since the antibody and the fluorescent labeling substance are loaded in the reaction parts in advance, the concentration of the target substance can be measured with simple operation by adding a sample containing a certain amount of the target substance and measuring the fluorescence polarization without performing addition operation of a reaction reagent.

(1) Target Substance

A target substance refers to a compound or composition to be measured by the support for fluorescence polarization immunoassay of the present disclosure. A measurable target substance is a compound, at least part of which can be used as an epitope to prepare an antibody. Examples include proteins, glycoproteins, peptides, polypeptides, oligonucleotides, polynucleotides, antibodies, antigens, haptens, hormones, drugs, enzymes, and receptors. Note that, for convenience of explanation, when the target substance is an antibody, it is described as a "test subject antibody."

The test subject antibody may be a monoclonal antibody, a multispecific antibody, a bifunctional antibody, a human antibody, a humanized antibody, an antibody derived from birds such as chickens, mammals such as humans and cows, non-primates such as camels, and other animals, a recombinant antibody, a chimeric antibody, a single-chain Fv ("scFv"), a single-chain antibody, a single-domain antibody, a Fab fragment, a F(ab') fragment, a F(ab')$_2$ fragment, a disulfide-linked Fv ("sdFv"), as well as, an anti-idiotypic ("anti-Id") antibody, a double domain antibody, a double variable domain antibody, or the like. When a target substance is classified by the origin or characteristics of the target substance, substances, such as a biological substance, a pharmaceutical substance, a viral substance, and a bacterial substance can also be measured. Biological substances include various components such as immunoglobulins that are produced by an organism in its body, various components that are discharged outside an organism, and an organism itself, in which organisms include plants and animals. Pharmaceutical substances include agricultural chemicals and the like, without limiting to the medicines that are prescribed to people or animals.

(2) Antibody for Measurement

The antibody loaded in the reaction parts of the support for fluorescence polarization immunoassay is an antibody that has an ability to bind to a target substance. The antibody is required to have the binding ability to recognize and bind to at least a part of the target substance as an epitope. If such an antibody is commercially available, a commercially available product can be used. If such an antibody is not commercially available, the antibody can be produced by using an immunogen in which an immunogen carrier material binds to a target compound via an acid amide bond or other group. The immunogen carrier material can be selected from conventional known ones. The immunogen carrier material can be any of an immunogenic protein, a polypeptide, a carbohydrate, a polysaccharide, a lipopolysaccharide, a nucleic acid and the like. Preferably, the immunogen carrier material is a protein or a polypeptide, more preferably, a bovine serum albumin (BSA), a keyhole limpet hemocyanin (KLH), and a thyroglobulin. Such immunogens can be used for preparation of polyclonal and monoclonal antibodies using a well-known method. Usually, an immunogen, preferably a mixture of an immunogen and an adjuvant, is injected at one or more various sites of a host animal, such as a rabbit, a goat, a mouse, a guinea pig, or a horse. An additional injection is made at the same or different sites at a regular or irregular interval. The titer is evaluated as appropriate to obtain the desired antibody. The antibody can be collected by sampling blood from the host animal.

Note that, to distinguish from the "test subject antibody," the antibody loaded in the reaction parts for measurement, which has the ability to bind to a target substance, is referred to as the "antibody for measurement". The antibodies for measurement include monoclonal antibodies, multispecific antibodies, bifunctional antibodies, human antibodies, humanized antibodies, antibodies derived from birds such as chickens, mammals such as humans and cows, non-primates such as camels, and other animals, recombinant antibodies, chimeric antibodies, single-chain Fv ("scFv"), single-chain antibodies, single-domain antibodies, Fab fragments, F(ab') fragments, F(ab')$_2$ fragments, disulfide-linked Fv ("sdFv"), as well as, anti-idiotypic ("anti-Id") antibodies, double domain antibodies, double variable domain antibodies, and the like. This is because an antibody is sufficient to bind to at least one epitope of a target compound. In addition, some of the amino acids may be replaced with other amino acid residues in the antibody for measurement prepared in this way for the purpose of improving heat resistance, chemical resistance, pressure resistance, or other purposes, without impairing the binding ability to the target substance.

(3) Fluorescent Labeling Substance

The fluorescent labeling substance loaded in the reaction parts is a compound that is obtained by labelling a target substance with a fluorescent dye.

The fluorescent dye is a dye that emits fluorescence. Each fluorescent dye has its own fluorescence life. In the present disclosure, a fluorescent dye having the fluorescence life of 1 to 10 nanoseconds, a fluorescent dye having the fluorescence life of over 10 nanoseconds to 200 nanoseconds, and a fluorescent dye having the fluorescence life of over 200 nanoseconds to 3,000 nanoseconds can be selected and used as appropriate, depending on the molecular weight of the target substance. Examples of the fluorescent dye having fluorescence life of 1 to 10 nanoseconds include indolenine, fluorescein compounds such as chlorotriazinylaminofluorescein, 4'-aminomethylfluorescein, 5-aminomethylfluorescein, 6-aminomethylfluorescein, 6-carboxyfluorescein, 5-carboxyfluorescein, 5- and 6-aminofluorescein, thioureafluorescein, and methoxytriazinylaminofluorescein, rhodamine derivatives such as rhodamine B, rhodamine 6G, and rhodamine 6GP, and, as registered trademark or product name, Alexa Fluor series such as Alexa Fluor 488, BODIPY series, DY series, ATTO series, Dy Light series, Oyster series, HiLyte Fluor series, Pacific Blue, Marina Blue, Acridine, Edans, Coumarin, DANSYL, FAN, Oregon Green, Rhodamine Green-X, NBD-X, TET, JOE, Yakima Yellow, VIC, HEX, R6G, Cy3, TAMRA, Rhodamine Red-X, Redmond Red, ROX, Cal Red, Texas Red, LC Red 640, Cy5, Cy5.5, and LC Red 705. Examples of the fluorescent dye having the fluorescence life of over 10 to 200 nanoseconds include naphthalene derivatives such as dialkylaminonaphthalenesulfonyl and pyrene derivatives such as N-(1-pyrenyl)maleimide, aminopyrene, pyrenebutanoic acid, and alkynylpyrene. Furthermore, examples of the fluorescent dye having the fluorescence life of over 200 to 3,000 nanoseconds include metal complexes such as platinum, rhenium, ruthenium, osmium, and europium.

A target substance can be labeled with a fluorescent dye, for example, by covalently binding the fluorescent dye to the target substance or by binding the fluorescent dye to the target substance via a suitable linker such as oligoethylene glycol or alkyl chain. The fluorescent dye has a functional group capable of binding to a carboxyl group, an amino group, a hydroxyl group, a thiol, a phenyl group, or the like. The target substance can be a protein or other substance that can be covalently bound to the above functional group. The fluorescent dye and the corresponding functional group of the target substance can be reacted under conditions known to those skilled in the art to produce a fluorescent labeling substance. After the reaction ends, the unreacted fluorescent dye may be removed by a conventional method. Note that the number of molecular bonds of a fluorescent dye introduced to a fluorescent labeling substance can be arbitrarily selected. One or more fluorescent dye molecules preferably bind to a single target substance molecule, and more preferably, two to five fluorescent dye molecules bind to a single target substance molecule. In the present disclosure, a fluorescent labeling substance in which a target substance is labeled with a fluorescent dye is simply referred to as the "fluorescent labeling substance."

(4) Support

As for the material of the support for fluorescence polarization immunoassay of the present disclosure, for example, polypropylene, polyethylene, polymethylpentene, ethylene-tetracyclododecene copolymer, polyacetal, acrylonitrile-butadiene-styrene resin, hydroxybenzoate polyester, polyetherimide, methacrylic resin, polyethylene terephthalate, polybutadiene terephthalate, polycyclohexylenedimethylene terephthalate, polyethylene naphthalate, polyacrylonitrile, polystyrene, polyamide, polycarbonate, polyvinyl alcohol, polylactic acid, or other resins, glass, quartz, or the like can be used. As for the support, various plates with multiple recesses, conventionally known as a microplate, a multi-well plate, a microwell plate, an immuno plate, and the like, used for various immunoassays, such as radioimmunoassays, enzyme immunoassays, and fluorescence immunoassays using fluorophores, can be used.

(5) Reaction Part

The recesses formed in the support can be used as reaction parts of the support for fluorescence polarization immunoassay of the present disclosure. The shape of the reaction part is not particularly limited, and may be a semicircular dish shape, a cylindrical shape (flat bottom), a disk shape, a hemispherical shape (U bottom), or the like. Likewise, the number of the reaction parts is not particularly limited, and at least two or more reaction parts may be present in the support. The number of the reaction parts is preferably 6 to 1,000, and more preferably, 10 to 100. Note that the size and shape of the support are not specifically limited and can be appropriately selected depending on the fluorescence polarization measuring instrument. Further, the arrangement of the reaction parts in the support is not particularly limited. If the support has reaction parts that are aligned vertically and horizontally, fluorescence polarizations of a large number of samples in small amounts can be effectively measured by using a microplate reader for detecting and measuring absorption, fluorescence, and luminescence. Note that the volume of a reaction part is 0.01 to 1 ml, preferably 0.1 to 0.4 ml, so that the reaction part can be loaded with an antibody for measurement and a fluorescent labeling substance and can receive a certain amount of sample solution containing a target substance.

FIG. 1 illustrates an example of a support for fluorescence polarization immunoassay 1. FIG. 1 illustrates a support 1 in which circular recesses are formed in three vertical and horizontal rows as reaction parts 3. An antibody for measurement and a fluorescent labeling substance are loaded in the reaction parts 3.

Figure 2:
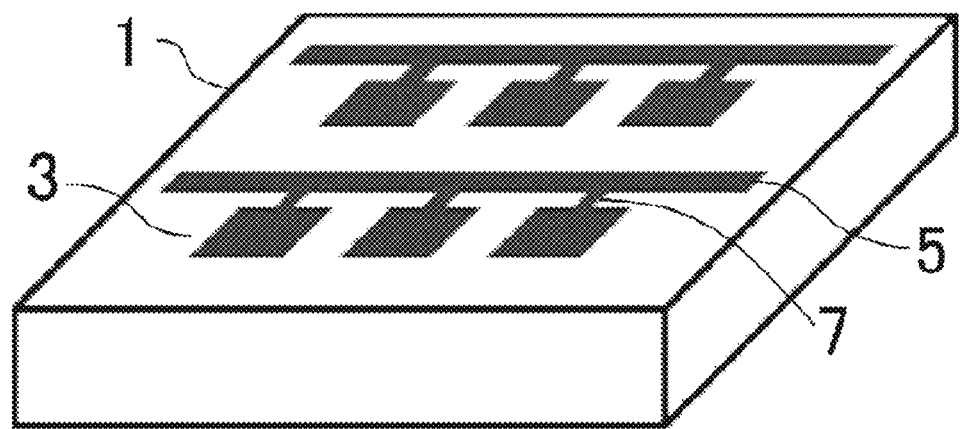
FIG. 2 is a diagram of a mode of the support for fluorescence polarization immunoassay, in which a series of reaction parts are connected through a linear communication path.
Figure 3A:
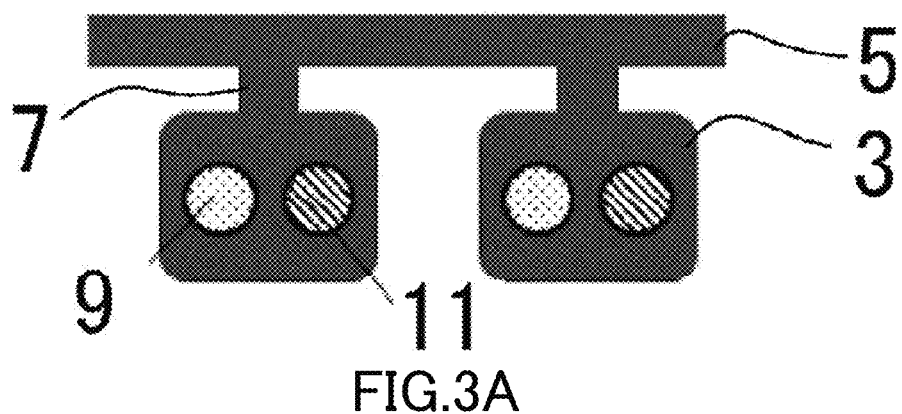
FIGS. 3A to 3C are diagrams for describing a usage of the support for fluorescence polarization immunoassay illustrated in FIG. 2.
Figure 3B:
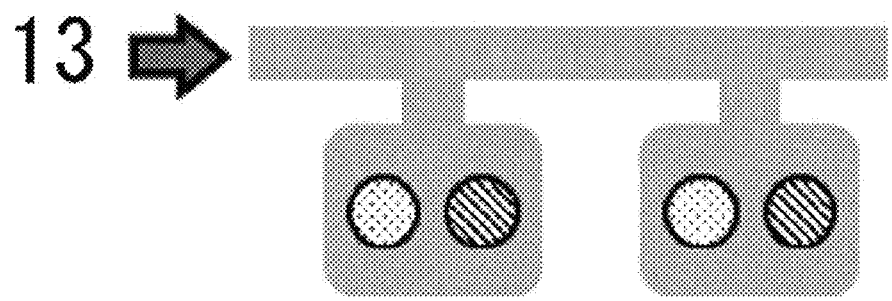
Figure 3C:
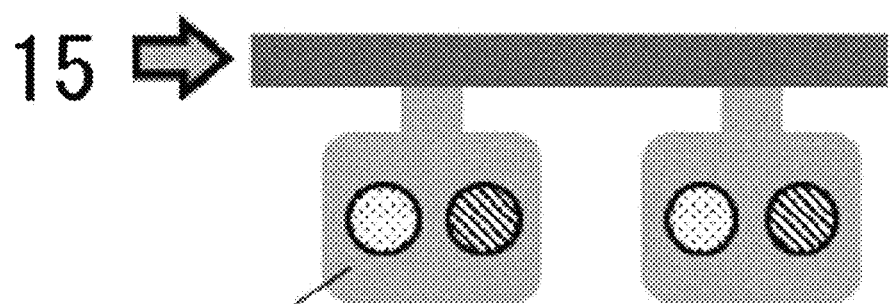

The plurality of reaction parts formed in the support for fluorescence polarization immunoassay may be connected to one another via a communication path. FIG. 2 illustrates a mode in which three square reaction parts 3 are connected in series via a linear communication path 5. In FIG. 2, branch paths 7 are stemming from the communication path 5. As illustrated in FIG. 3A, the plurality of reaction parts 3 loaded with a fluorescent labeling substance 9 and an antibody for measurement 11 are connected to the communication path 5 via branch paths 7 leading to the respective reaction parts 3. The communication path 5 can be used as a sample solution injection path. When a sample solution 13 is injected from the left end of the communication path 5 as illustrated in FIG. 3B, the three reaction parts 3 can be filled with the sample solution 13 through one operation. As illustrated in FIG. 3C, after filling the sample solution 13, the sample solution 13 can be removed from the communication path 5 by feeding a sealing agent 15 such as air, nitrogen gas, or other gases that do not affect fluorescence polarization measurement, instead of the sample solution 13. Instead of air or other gases, a liquid that does not affect fluorescence polarization measurement, such as silicone, fluorinated inert liquid, or the like, may be fed as a sealing agent 15.

Figure 4:
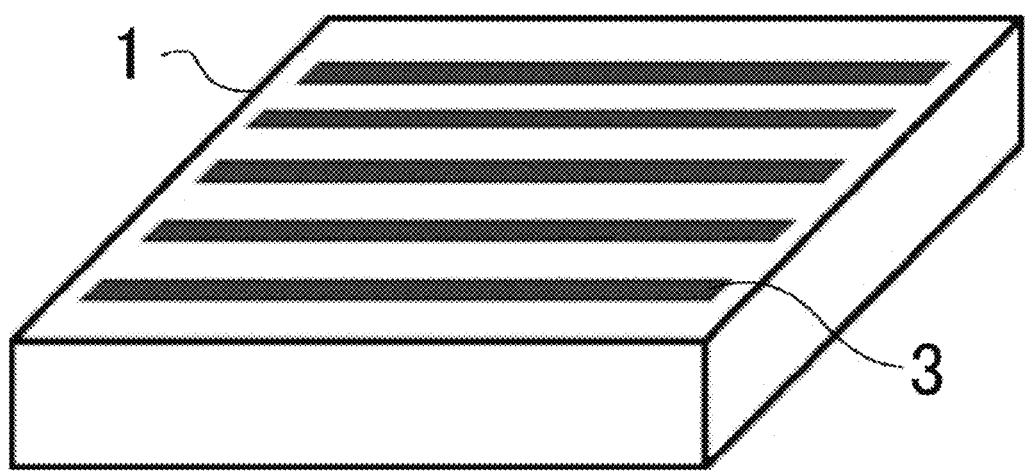
FIG. 4 is a diagram of the support for fluorescence polarization immunoassay with five microfluidic channels as the reaction parts.

Further, polydimethylsiloxane (PDMS) microfluidic channels can be used as reaction parts of the support for fluorescence polarization immunoassay. FIG. 4 illustrates a support 1 having five microfluidic channels as reaction parts 3.

(6) Loading

The reaction parts of the support for fluorescence polarization immunoassay are loaded with an antibody for measurement and a fluorescent labeling substance. The term "loaded" herein refers to a state in which an antibody for measurement and a fluorescent labeling substance are bound in a way that, when a sample solution containing a target substance is added to the reaction parts, the antibody for measurement and the fluorescent labeling substance can be released from the surface of the reaction parts into the solution. Therefore, those cases in which an antibody for measurement and the like are immobilized to the reaction parts by a covalent bond are not included. Also excluded are those cases in which the reaction parts underwent plasma treatment or other surface treatment to enhance the binding force of an antibody for measurement or a fluorescent labeling substance so that the antibody for measurement or the fluorescent labeling substance cannot be released from the surface of the reaction parts even when a sample solution is added.

The method of loading an antibody for measurement or a fluorescent labeling substance in the reaction parts is not particularly limited. For example, a solution containing a dissolved or dispersed antibody for measurement and a solution containing a dissolved or dispersed fluorescent labeling substance are respectively dropped into the reaction parts and dried by freeze-drying, vacuum drying, thermal drying, low-temperature drying or the like, whereby the antibody for measurement and fluorescent labeling substance can be loaded in the reaction parts. A mixed solution of antibody for measurement and fluorescent labeling substance dissolved or dispersed in specific ratios may be prepared in advance, dropped into the reaction parts, and loaded by freeze-drying or the like as described above.

(7) Fluorescence Polarization Immunoassay

The fluorescence polarization immunoassay utilizes competitive reactions of substances and a change in polarization caused by a change in molecular weights of the competitive substances. When a fluorescent dye in a liquid maintains a steady state in an excited state, the fluorescent dye emits polarized fluorescence in the same plane, but, when a fluorescent dye rotates in an excited state due to Brownian motion, the fluorescent dye emits fluorescence in a plane different from the excitation plane, thus eliminating the fluorescence polarization. A fluorescence polarization indicates the degree of rotation of fluorescent molecules between the time the molecules are excited and the time the molecules emit fluorescence. Low molecular weight molecules rotate violently in solution due to Brownian motion, resulting in low polarization, while large molecular weight molecules have weak Brownian motion, resulting in increased polarization. For example, in a solution containing a mixture of target substance A, antibody B that have a specific binding ability to the target substance A, and fluorescent labeling substance C in which the target substance A is labeled with a fluorescent dye, the target substance A, the antibody B, and the fluorescent labeling substance C react competitively in the solution. Thus, a high concentration of the target substance A increases the amount of binding between the target substance A and the antibody B and increases the amount of free fluorescent labeling substance C that does not bind to the antibody B. If there is a difference between the mass of the fluorescent labeling substance C and the mass of the conjugate of the antibody B and the fluorescent labeling substance C, the concentration of the target substance A can be measured using a change in polarization as an indicator.

(8) Loaded Amount

As described above, since the fluorescence polarization immunoassay utilizes competitive reactions of a target substance, an antibody for measurement, and a fluorescent labeling substance, if the loaded amounts of the fluorescent labeling substance or the antibody for measurement are different, the fluorescence polarization changes, and the width of the measurable range of the target substance also changes. In the support for fluorescence polarization immunoassay of the present disclosure, the plurality of reaction parts may have different loaded amounts of a fluorescent labeling substance and an antibody for measurement for respective reaction parts. With such a support with different loaded amounts, the loaded amounts can be easily changed by changing the amount of solutions of a fluorescent labeling substance and an antibody for measurement to be dropped into the reaction parts, or by changing the concentrations of these solutions to be dropped.

Figure 5:
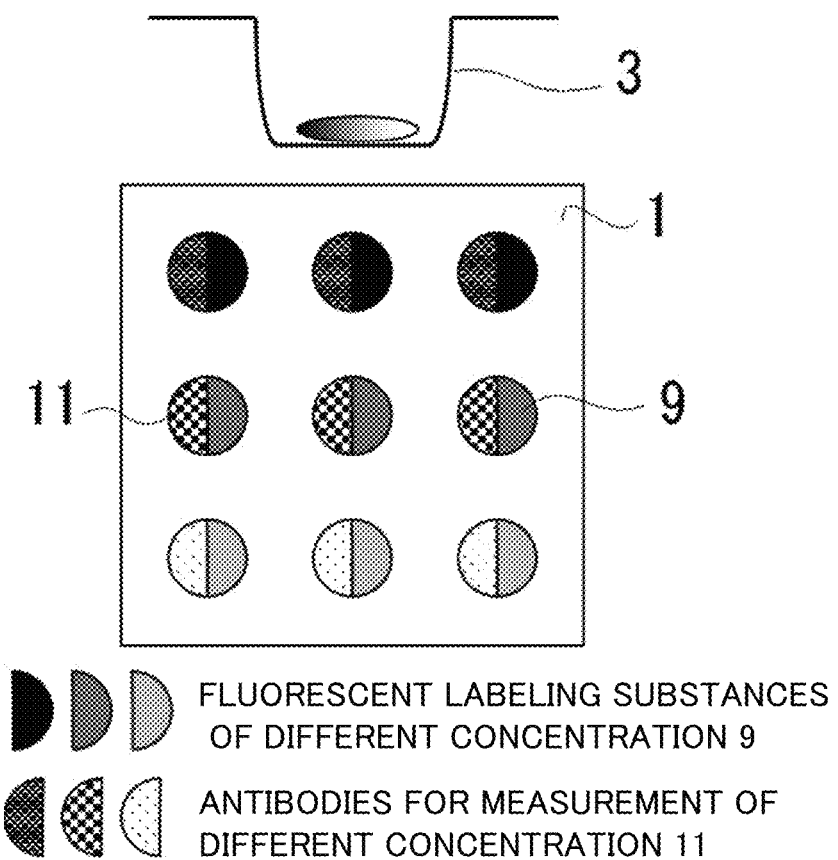
FIG. 5 is a diagram of the support for fluorescence polarization immunoassay, in which the reaction parts are aligned in a 3×3 configuration, and each reaction part is loaded with a different concentration of a fluorescent labeling substance and a different concentration of an antibody.

As one example, FIG. 5 schematically illustrates a mode, in which reaction parts 3 are aligned in a 3×3 configuration in the support 1, and each reaction part 3 is loaded with a different concentration of a fluorescent labeling substance 9 and a different concentration of an antibody for measurement 11. Note that, although FIG. 5 illustrates a mode in which the loaded amounts of both the fluorescent labeling substance 9 and the antibody for measurement 11 change, the loaded amount of only one of the fluorescent labeling substance 9 and the antibody for measurement 11 may change. The loaded amount can be appropriately selected according to the characteristics of the target substance and the like.

For example, when the loaded amount of all the fluorescent labeling substance in a horizontal row m1 of reaction parts arranged in vertically n×horizontally m is Dm1, and the loaded amount of the fluorescent labeling substance in a horizontal row m2 is Dm2, creation of a calibration curve and measurement of a sample solution can be simultaneously performed under a condition of the loaded amounts of the fluorescent labeling substance Dm1 and Dm2. Even when the concentration of a target substance in a sample solution is unknown, the concentration can be measured using one of the calibration curves, which increases the width of the measurement range, and in turn deceases the dilution process of the sample solution.

(9) Antibody with Different Binding Affinity

The antibodies for measurement may be antibodies having different binding affinities for a target substance. The width of the measurement range can also be increased by using antibodies having different binding affinities.

The fluorescence polarization immunoassay can be considered as an antigen-antibody reaction if the target substance is an antigen. The equilibrium calculation formula of binding in the antigen-antibody reaction can be expressed as Ka=([AgAb])/([Ag][Ab]) and B/F=([AgAb])/[Ag] where Ag: antigen concentration, Ab: antibody concentration, Ka: binding constant, B: bound concentration, and F: free concentration.

If the initial input concentrations of Ag and Ab are p and q, then [Ag]=p−[AgAb], [Ab]=q−[AgAb], and $(B/F)^2+(B/F)(1+Kap-Kaq)-Kaq=0$.

When the concentration of the target substance is defined as x and x=[Ag], and the concentration of the fluorescent labeling substance is defined as p, and p is replaced as p→p+x, a ternary notation $(B/F)^2+(B/F)(1+Kap+Kax-Kaq)-Kaq=0$ can be represented as B/F (Ka, p, x, q). Assuming that (B/F)=R, the above equation can be transformed into $R(Ka, p, x, q)=-(1+Kap+Kax+(-Ka)q)/2+\sqrt{((1+Kap+Kax+(-Ka)q)^2+4Kaq))}/2$.

When the fluorescence polarization of the fluorescent labeling substance is Fh when bound and Fl when free, the value of the fluorescence polarization can be expressed as a variable in the following equation (1):

$$f(Ka, p, x, q) = \frac{FhR(Ka, px, q) + Fl}{1 + R(Ka, p, x, q)} \quad [\text{Math. 1}]$$

Figure 6:
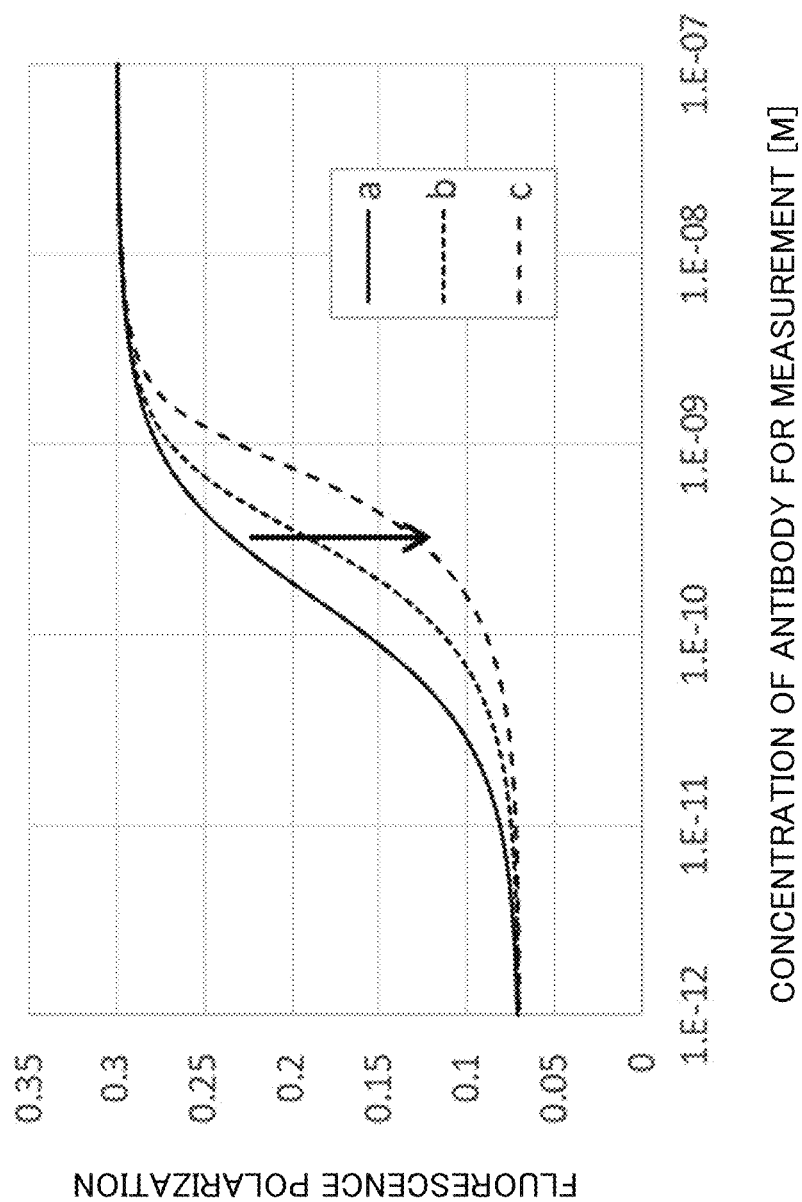
FIG. 6 is a diagram illustrating the result of measuring a fluorescence polarization against the concentration of an antibody for measurement by changing the concentration of a target substance.

FIG. 6 illustrates the result of plotting the above equation (1) by changing the concentration of an antibody for measurement when the concentration of a fluorescent labeling substance and the binding constant of the antibody for measurement are the same where the binding constant $Ka=1\times10^{10}$ $M^{-1}$, $Fh=0.3$, $Fl=0.07$ under a condition indicated in Table 1 with three kinds of concentrations of a target substance. As indicated by curves a, b, and c, the fluorescence polarization decreases as the concentration of the target substance increases.

TABLE 1

| Curve | Ka | Fluorescent labeling substance (p) | Target substance (x) |
|---|---|---|---|
| a | $1 \times 10^{10} M^{-1}$ | $1 \times 10^{-10} M$ | 0M |
| b | $1 \times 10^{10} M^{-1}$ | $1 \times 10^{-10} M$ | $3 \times 10^{-10} M$ |
| c | $1 \times 10^{10} M^{-1}$ | $1 \times 10^{-10} M$ | $1 \times 10^{-9} M$ |

Figure 7:
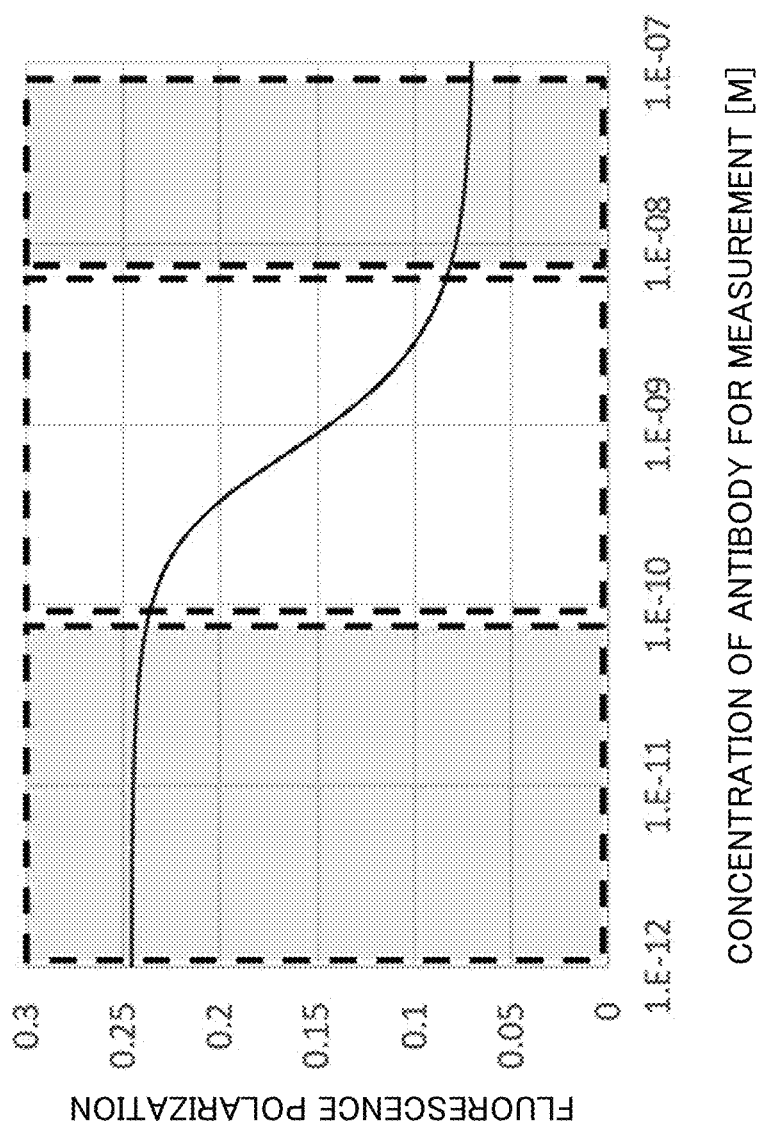
FIG. 7 is a diagram illustrating the result of measuring a fluorescence polarization against a target substance with a fluorescent labeling substance and the target substance being kept constant.

On the other hand, FIG. 7 illustrates the result of measuring the fluorescence polarization against the concentration of an antibody for measurement when the concentration of a target substance is constant ($q=4\times10^{-10}$ M) and the concentration of a fluorescent labeling substance is also constant (concentration $p=1\times10^{-10}$ M). FIG. 7 indicates that there is a certain correlation between the antibody for measurement and the fluorescence polarization in the range of $1\times10^{-10}$ M to $1\times10^{-8}$ M, which is outlined by a broken line, and this range is the measurement range of the target substance. This result is consistent with the fact that the width of the measurement range increases when the loaded amount of the antibody for measurement in the reaction parts changes.

Figure 8:
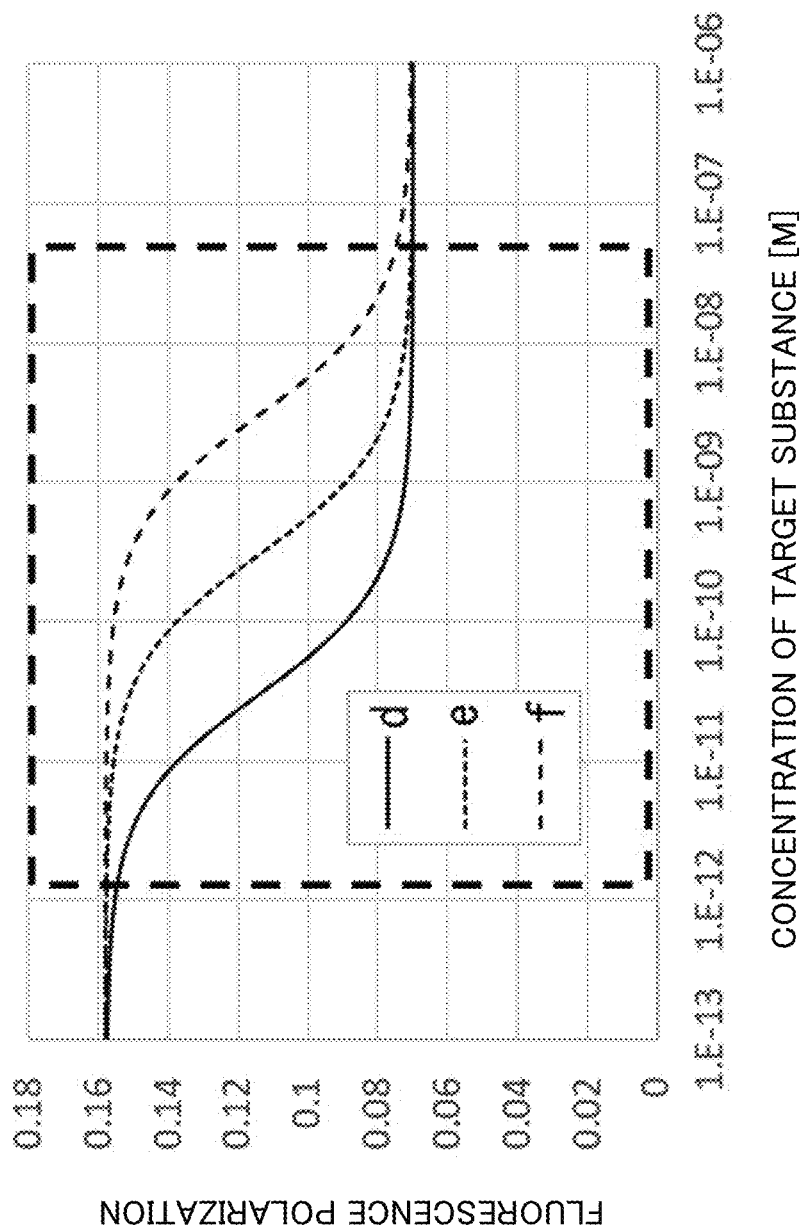
FIG. 8 is a diagram illustrating the result of measuring a fluorescence polarization against the concentration of a target substance, using antibodies for measurement with different binding constants.

Next, FIG. 8 illustrates the result of creating fluorescence polarization curves in the same way as above using antibodies for measurement with different binding constants Ka and changing the concentrations of the antibodies for measurement and the concentration of a fluorescent labeling substance as illustrated in Table 2. The measurable range differs depending on the curve, in which the measurable range of the target substance is the range of $1\times10^{-11}$ M to $1\times10^{-10}$ M with curve d, the range of $1\times10^{-10}$ M to $1\times10^{-9}$ M with curve e, the range of $1\times10^{-9}$ M to $1\times10^{-8}$ M with curve f In the present disclosure, by loading antibodies with different binding affinities for a target substance in the reaction parts, as well as, by changing the concentration of a fluorescent labeling substance and the concentration of the antibodies for measurement that are loaded in the reaction parts, for example, the range outlined by a broken line in FIG. 8 can be defined as the measurement range width.

TABLE 2

| Curve | Ka | Fluorescent labeling substance (p) | Target substance (x) |
|---|---|---|---|
| d | $1 \times 10^{11} M^{-1}$ | $1 \times 10^{-11} M$ | $1 \times 10^{-11} M$ |
| e | $1 \times 10^{10} M^{-1}$ | $1 \times 10^{-10} M$ | $1 \times 10^{-10} M$ |
| f | $1 \times 10^{9} M^{-1}$ | $1 \times 10^{-9} M$ | $1 \times 10^{-9} M$ |

Figure 9:
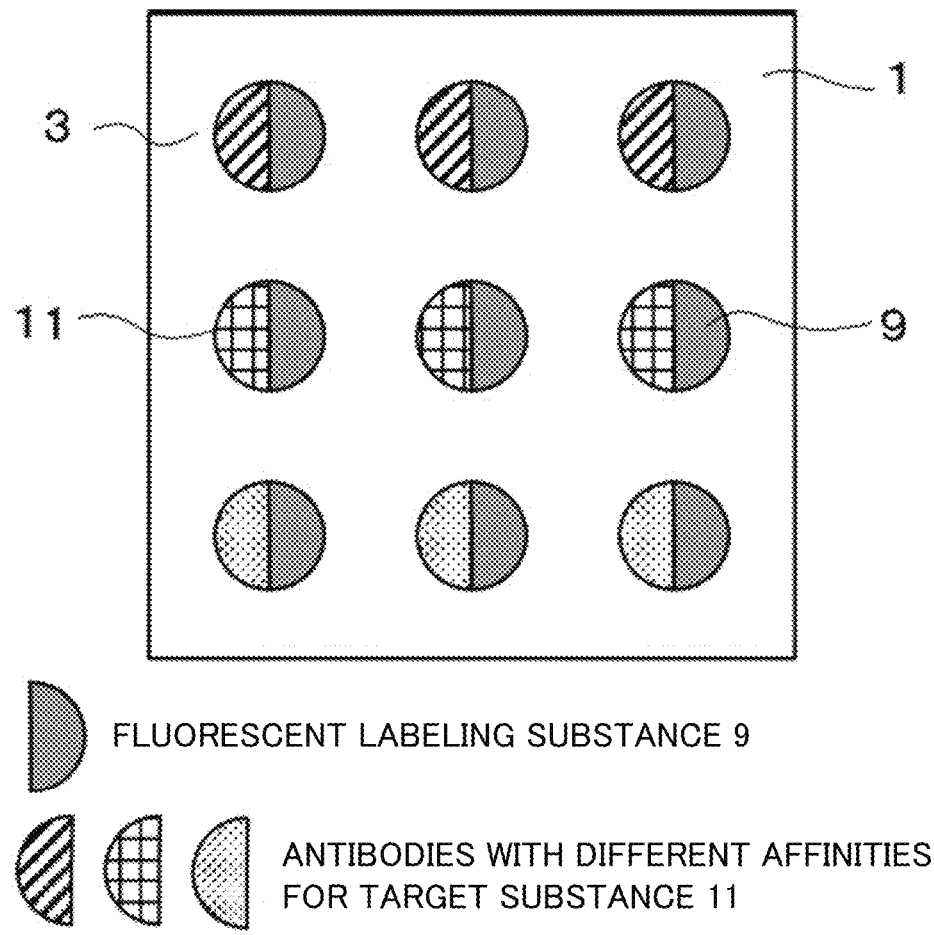
FIG. 9 is a diagram of the support for fluorescence polarization immunoassay, in which different fluorescent labeling substances and antibodies with different binding affinities for a target substance are loaded in 3×3 reaction parts.

FIG. 9 schematically illustrates a mode of a support in which a fluorescent labeling substance 9 and antibodies (antibodies for measurement) 11 having different binding affinities for a target substance are loaded in the support 1 having 3×3 reaction parts 3. Note that, for example, antibodies with different binding affinities for a target substance can be prepared by inoculating an immunogen, which is a compound to be measured that is bound to an immunogen carrier material such as polysaccharide, into one or more various sites of a host animal such as a rabbit or other host animals to obtain antibodies, evaluating the titer as appropriate, and collecting antibodies with different titers.

(10) pH Adjuster

Figure 10:
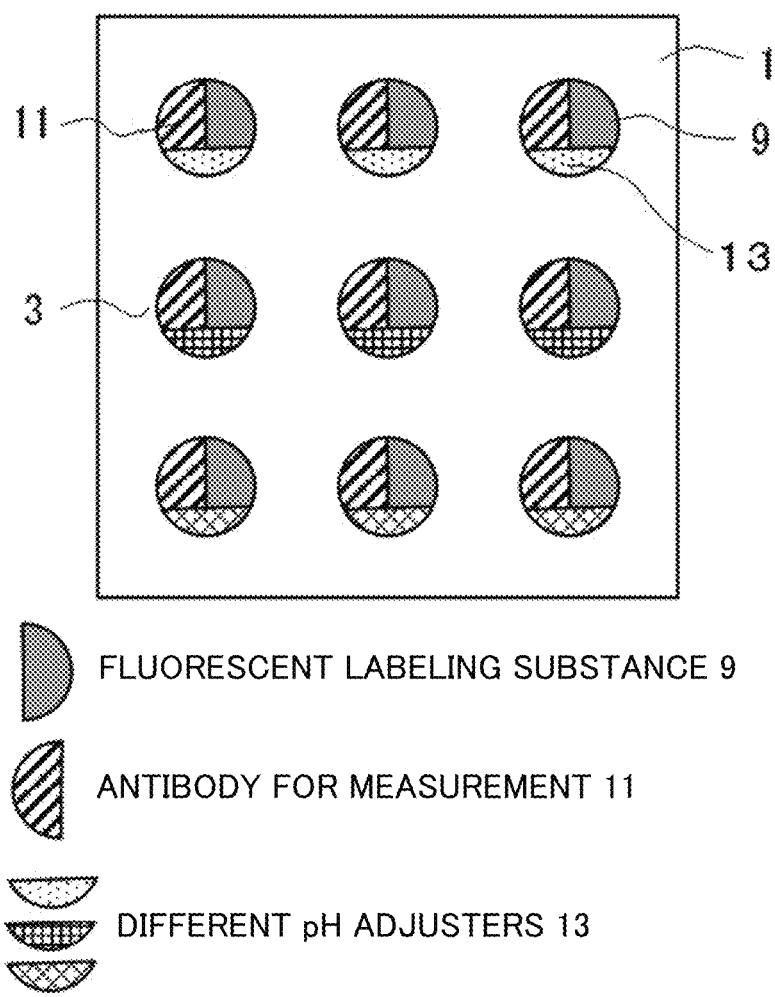
FIG. 10 is a diagram of the support for fluorescence polarization immunoassay, in which certain amounts of a fluorescent labeling substance and an antibody for measurement are loaded in each of 3×3 reaction parts, and a different pH adjuster is further loaded in each row.

A pH adjuster may further be loaded in the reaction parts. Since the binding affinity between a target substance and an antibody for measurement changes depending on pH, an increased width of the measurement range can be secured. Examples of such a pH adjuster include, Glycine-NaOH (pKa 9.60), Tris-HCl (pKa 8.20), Tricine-HCl (pKa 8.15), HEPES-NaOH (pKa 7.55), $NaH_2PO_4$—$Na_2HPO_4$ (pKa 7.22), MOPS-NaOH (pKa 7.20), MES-NaOH (pKa 6.15), Acetate-NaOH (pKa 4.80), Glycine-NaOH (pKa 2.34), and GTA buffer. The pH adjuster can be loaded in the reaction parts by preparing a solution of such a pH adjuster, dropping the solution into the reaction parts and drying the solution in the same manner as loading the fluorescent labeling substance or the antibody for measurement. Note that the pH adjuster can be selected appropriately according to the characteristics of the target substance, the fluorescent labeling substance, and the antibody for measurement. FIG. 10 schematically illustrates a mode in which certain amounts of a fluorescent labeling substance and an antibody for measurement are loaded in reaction parts aligned in 3×3, and a different pH adjuster is further loaded for each row.

(11) Fluorescence Polarization Immunoassay Kit

The support for fluorescence polarization immunoassay of the present disclosure can be used as a fluorescence polarization immunoassay kit, which further includes a solvent for dissolving a target substance.

Examples of solvents for dissolving the target substance include: water such as pure water; alcohols such as methanol, ethanol, and butanol; ketones such as acetone, diethyl ketone, and methyl amyl ketone; alkanes such as hexane and heptane; ethers such as diethyl ether; methyl sulfoxide, acetonitrile, chloroform and mixed solvents thereof.

(12) Measurement Method

Using the support for fluorescence polarization immunoassay of the present disclosure, a target substance contained in a sample solution can be analyzed as follows.

First, a sample solution is prepared by dissolving or dispersing a target substance in pure water or other solvent for dissolving the target substance and removing foreign substances contained in the solution by filtration or other means as necessary. A certain amount of the sample solution is added to each of the reaction parts of the support for fluorescence polarization immunoassay. In this way, the antibody for measurement and fluorescent labeling substance loaded in the reaction parts react with the target substance contained in the sample solution. Since the reaction is based on an antigen-antibody reaction, the reaction is rapid and reproducible, and the reaction parts contain the conjugate of the target substance and the antibody for measurement, the conjugate of the fluorescent labeling substance and the antibody for measurement, and the like. When the concentration of the target substance contained in the sample solution is high, the amount of binding between the target substance and the antibody for measurement increases, and the amount of free fluorescent labeling substance that does not bind to the antibody for measurement increases. In the fluorescence polarization immunoassay, a change in molecular weight attributed to the binding between the fluorescent labeling substance and the target substance is measured as a temporal change in molecular orientation. When there is a difference between the mass of the fluorescent labeling substance and the mass of the conjugate of the antibody for measurement and the fluorescent labeling substance, the concentration of the target substance can be measured using a change in polarization as an indicator. The measurement of fluorescence polarization can be obtained using an arbitrary polarization measurement instrument. The fluorescence polarization is measured at a predetermined time after the reaction ends. The measurement should be carried out at a constant temperature within the range of 4 to 40° C., preferably 10 to 40° C., which is a range within which the target substance does not denature. A target substance can be quantified by creating a calibration curve in advance by operating in the same way as described above using a solution containing the target substance of a known concentration and comparing with the measured value of a sample solution.

Figure 11:
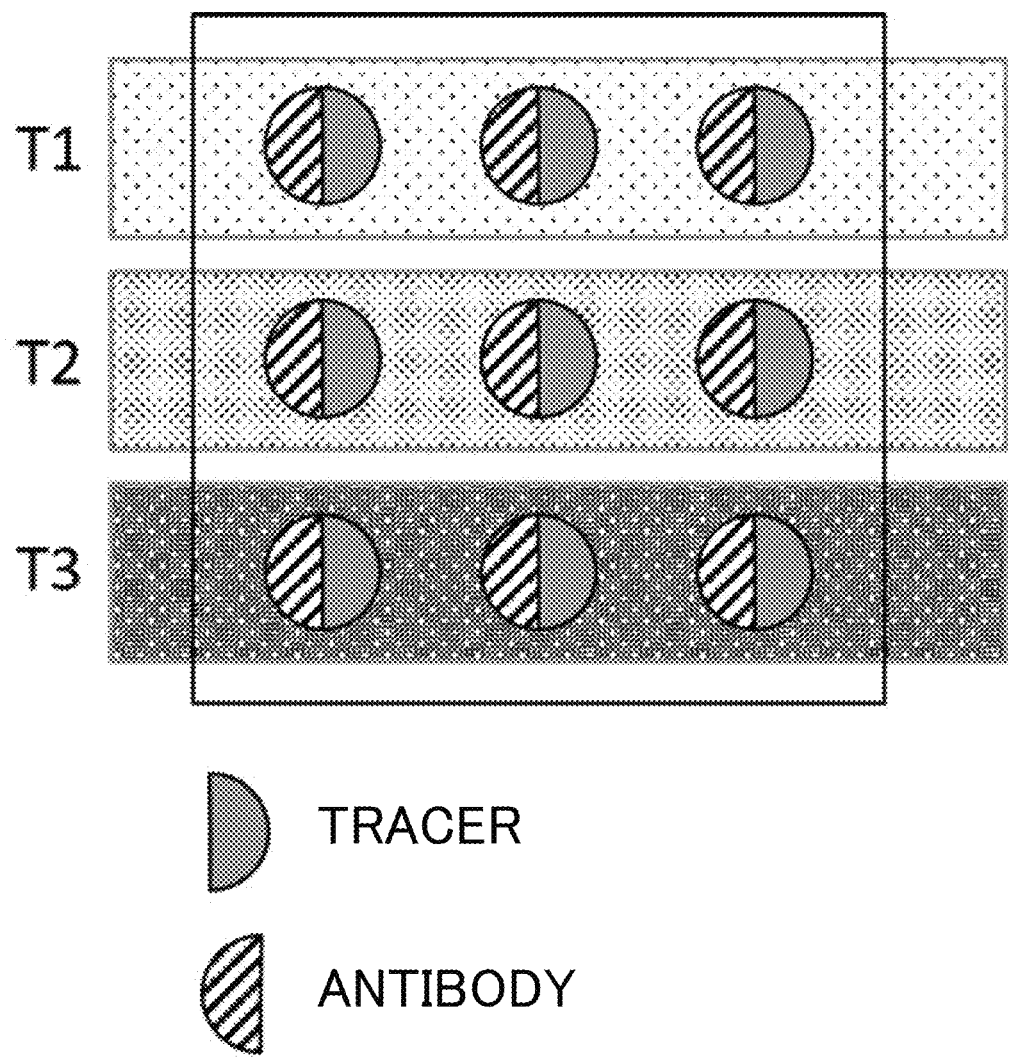
FIG. 11 is a diagram illustrating a mode of measuring the reaction parts of the support for fluorescence polarization immunoassay at different temperatures T1, T2, and T3.

On the other hand, for example, when a calibration curve is created at a temperature of 10° C. and the fluorescence polarization of a target substance contained in the sample solution is measured, there may be a case in which measurement may not fall within the measurement range using this calibration curve depending on the concentration of the target substance contained. In such a case, the measurement temperature can be changed to 40° C. and measurement can be conducted at a predetermined time after the reaction. Since the binding constant changes according to a temperature, a wide measurement range can be secured by changing a temperature. FIG. 11 schematically illustrates a mode in which the reaction parts are measured at temperatures T1, T2, and T3.

In the present disclosure, the instrument is not limited as long as fluorescence polarizations can be measured. As described above, when a support for fluorescence polarization immunoassay, in which reaction parts are configured as microfluidic channels, is used, highly sensitive measurement can be performed using a small amount of sample by using a measuring instrument capable of measuring the microfluidic channels.

Embodiments

The following will specifically describe the present disclosure with embodiments, while these embodiments should not be construed as limiting the present disclosure in any way.

Embodiment 1

Figure 12:
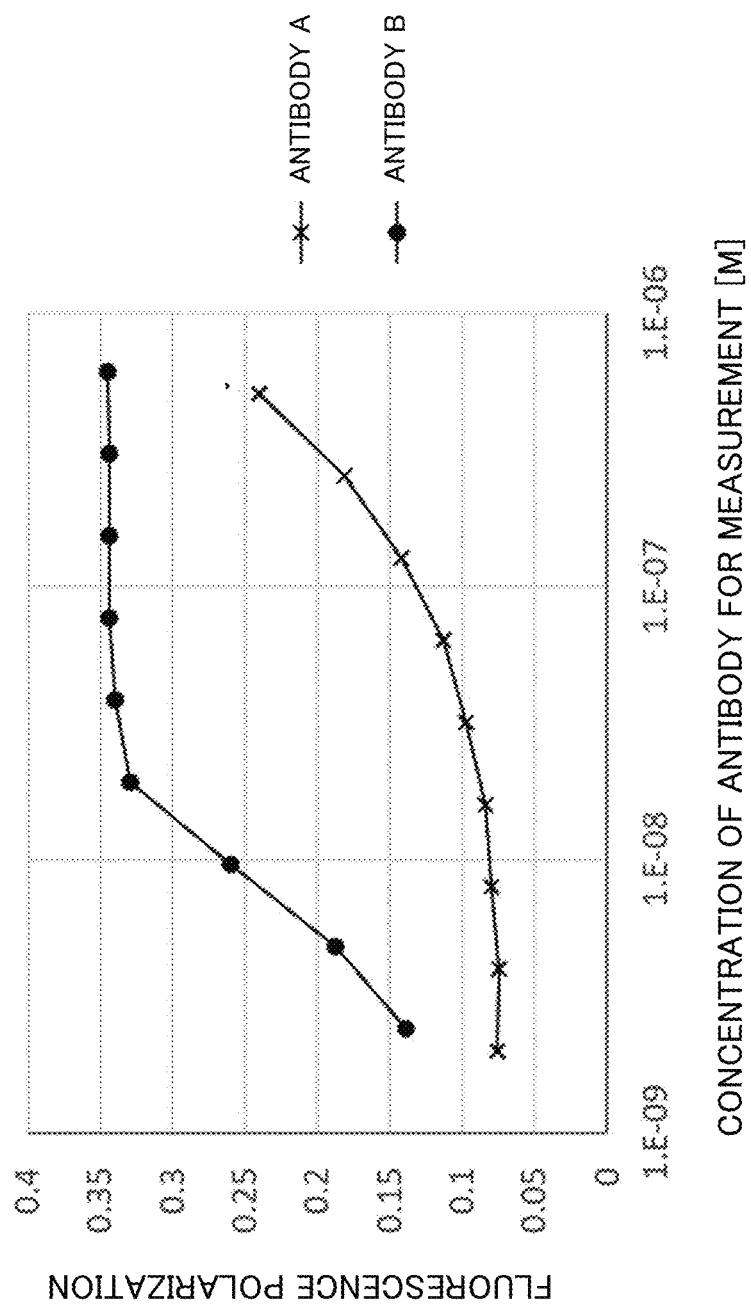
FIG. 12 is a diagram illustrating the result of Example 1, which illustrates the result of measuring a fluorescence polarization against the concentration of an antibody for measurement using antibodies for measurement with different binding constants.

Antibody for measurement A of binding constant Ka=2× $10^6$ $M^{-1}$ and antibody for measurement B of binding constant Ka=3×$10^8$ $M^{-1}$ were used. Solutions with the antibody for measurement A diluted at $5\times10^{-7}$ M, $3\times10^{-7}$ M, $1\times10^{-7}$ M, $6\times10^{-8}$ M, $3\times10^{-8}$ M, $2\times10^{-8}$ M, $8\times10^{-9}$ M, $4\times10^{-9}$ M and $2\times10^{-9}$ M, and solutions with the antibody for measurement B diluted at $6\times10^{-7}$ M, $3\times10^{-7}$ M, $1\times10^{-7}$ M, $8\times10^{-8}$ M, $4\times10^{-8}$ M, $2\times10^{-8}$ M, $1\times10^{-8}$ M, $5\times10^{-9}$ M, and $2\times10^{-9}$ M were prepared. The antibody for measurement A or antibody for measurement B of each concentration is reacted with a solution containing a fluorescent labeling substance at the concentration of $1\times10^{-8}$ M and the fluorescence polarization was measured. The result is illustrated in FIG. 12. Different fluorescence polarization curves were obtained by using antibodies for measurement having different binding constants.

Figure 13:
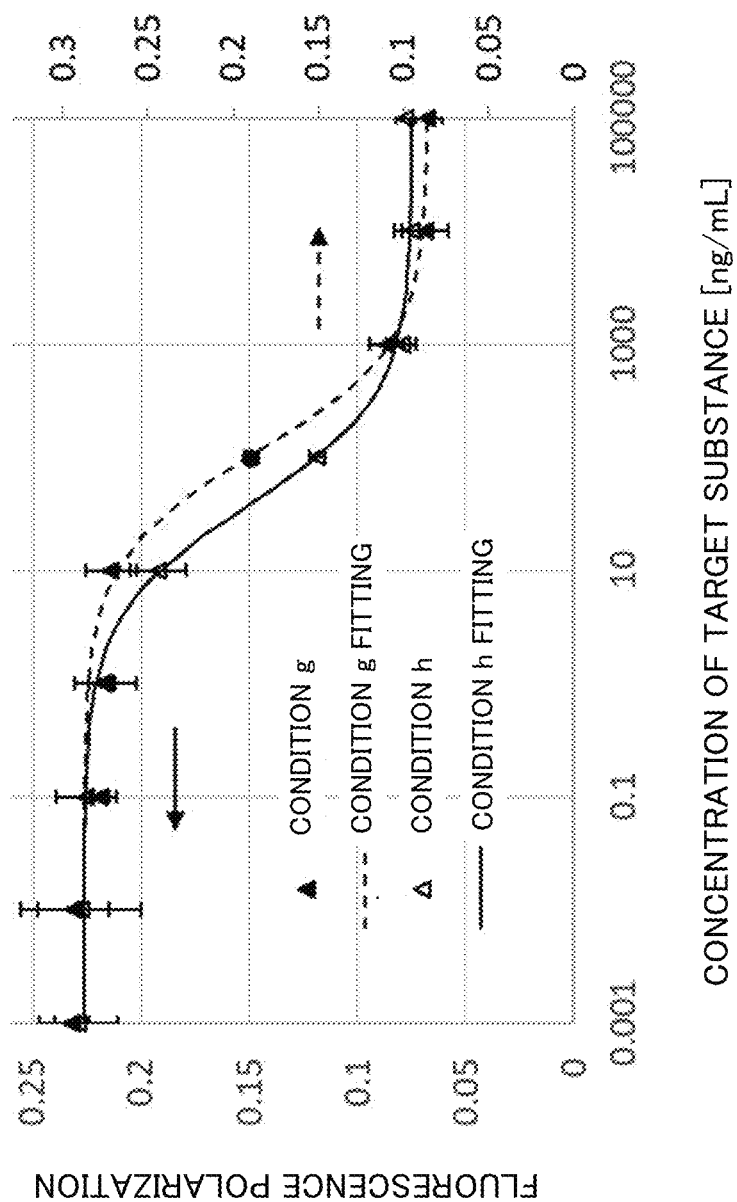
FIG. 13 is a diagram illustrating the result of Example 1, which illustrates the result of measuring a fluorescence polarization against the concentration of a target substance, using antibodies for measurement with different binding constants.

Next, as illustrated in Table 3, a fluorescent labeling substance was loaded in each reaction part so that the concentration becomes $4.5\times10^{-9}$ M, and the antibody for measurement A (binding constant $Ka=2\times10^{6}$ M$^{-1}$) was loaded in the reaction part g so that the concentration becomes $5\times10^{-7}$ M, and the antibody for measurement B ($Ka=3\times10^{8}$ M$^{-1}$) was loaded in the reaction part h so that the concentration becomes $1\times10^{-8}$ M to prepare a support. Using this support, certain amounts of different concentrations of a target substance, 0.001 ng/ml, 0.01 ng/ml, 0.1 ng/ml, 1 ng/ml, 10 ng/ml, 100 ng/ml, 1000 ng/ml, 10,000 ng/ml, and 100,000 ng/ml, were added in the reaction part g and the reaction part h and the fluorescence polarization was measured. The result is illustrated in FIG. 13. As illustrated in FIG. 13, the concentration of the target substance at the lower quantification limit on curve g where the antibody for measurement A was loaded was 16 ng/ml, and the concentration of the target substance at the upper quantification limit was $2.7\times10^{3}$ ng/ml. On the other hand, the concentration of the target substance at the lower quantification limit on curve h where the antibody for measurement B was loaded was 4.1 ng/ml, and the concentration of the target substance at the upper quantification limit was $1.5\times10^{3}$ ng/ml. By loading antibodies for measurement having different binding constants in the support, the target substance was able to be measured in different measurement ranges.

TABLE 3

| Reaction part | Ka | Fluorescent labeling substance | Antibody for measurement |
|---|---|---|---|
| g | $2\times10^{6}$M$^{-1}$ | $4.5\times10^{-9}$M | $5\times10^{-7}$M |
| h | $3\times10^{8}$M$^{-1}$ | $4.5\times10^{-9}$M | $1\times10^{-8}$M |

Embodiment 2

Figure 14:
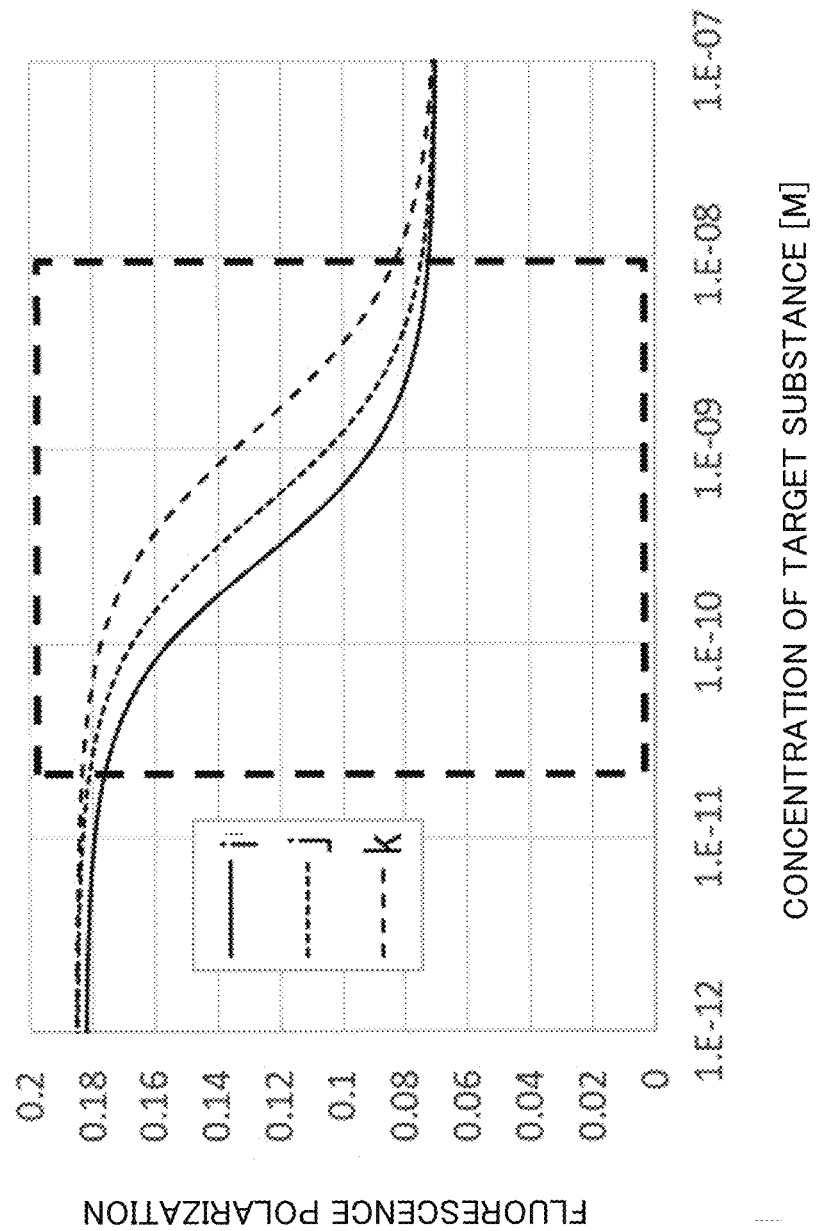
FIG. 14 is a diagram illustrating the result of measuring a fluorescence polarization against the concentration of a target substance, using a support loaded with different concentrations of a fluorescent labeling substance and an antibody for measurement.

A fluorescent labeling substance and an antibody for measurement where $Ka=1\times10^{10}$ M$^{-1}$ were loaded in reaction parts i, j, and k at the concentrations illustrated in Table 4, then, certain amounts of sample solutions containing different concentrations of a target substance were added to these reaction parts. The fluorescence polarization was calculated according to the following equation. Note that Fh=0.3 and Fl=0.07 were defined. The result is illustrated in FIG. 14.

$$f(Ka, p, x, q) = \frac{FhR(Ka, px, q) + Fl}{1 + R(Ka, p, x, q)} \quad \text{[Math. 2]}$$

TABLE 4

| Reaction part | Fluorescent labeling substance | Antibody for measurement |
|---|---|---|
| i | $1\times10^{-11}$M | $1\times10^{-10}$M |
| j | $2\times10^{-10}$M | $2\times10^{-10}$M |
| k | $1\times10^{-9}$M | $6\times10^{-10}$M |

Curves i, j, and k were obtained according to the loaded amounts of the fluorescent labeling substance and the antibody for measurement. It was found that each measurement range was different, and measurement was possible without diluting a sample solution within the range outlined by a broken line in FIG. 14.

Next, using an antibody for measurement having a binding constant $Ka=3\times10^{8}$ M$^{-1}$, reaction parts m and n illustrated in Table 5 were prepared. Certain amounts of sample solutions containing different concentrations of a target substance were added to these reaction parts, and the fluorescence polarization was measured. The result is illustrated in FIG. 15.

TABLE 5

| Reaction part | Fluorescent labeling substance | Antibody for measurement |
|---|---|---|
| m | $4.5\times10^{-9}$M | $1\times10^{-8}$M |
| n | $9\times10^{-10}$M | $1\times10^{-8}$M |

Figure 15:
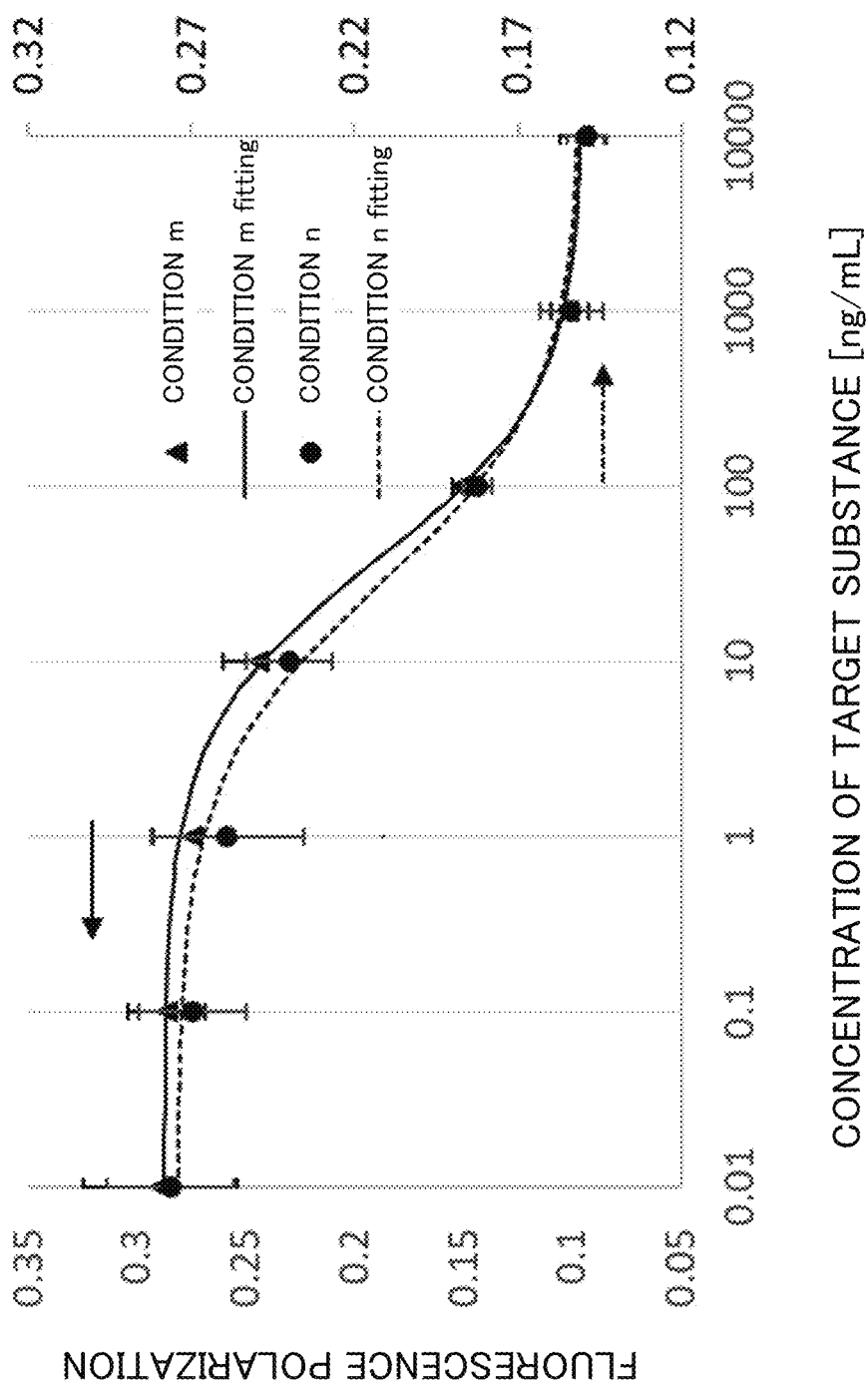
FIG. 15 is a diagram illustrating the result of measuring a fluorescence polarization against the concentration of a target substance by changing the concentration of a fluorescent labeling substance.

As illustrated in FIG. 15, the concentration at the lower quantification limit on curve m was 4.1 ng/ml, and the concentration at the upper quantification limit on curve m was $1.5\times10^{3}$ ng/ml. On the other hand, the concentration of the target substance at the lower quantification limit on curve m was 2 ng/ml, and the concentration at the upper quantification limit was $2.4\times10^{2}$ ng/ml. By loading different concentrations of a fluorescent labeling substance in the support, a target substance can be measured in different measurement ranges.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

What is claimed is:

1. A support for fluorescence polarization immunoassay of a target substance in a sample, the support comprising:
    multiple recesses, the recesses being loaded with an antibody having a binding ability to the target substance and a fluorescent labeling substance in which the target substance is labeled with a fluorescent dye,
    wherein the support comprises a plurality of types of the recesses resulting from difference in a loaded amount of the antibody and/or difference in a loaded amount of the fluorescent labeling substance,
    wherein the support comprises multiple groups each including multiple homogeneous recesses, the multiple homogeneous recesses being loaded with a same substance and having a same loaded amount, and wherein the antibody and the fluorescent labeling substance are bound to a surface of the recesses in a way that, when a sample solution containing the target substance is added to the recesses, the antibody and the fluorescent labeling substance can be released from the surface of the recesses into the sample solution.

2. The support for fluorescence polarization immunoassay according to claim 1, wherein the recesses are microfluidic channels.

3. The support for fluorescence polarization immunoassay according to claim 1, wherein some of the recesses are connected through a communication path and a branch path,
wherein the branch path connects some of the recesses with the communication path, and
wherein some of the recesses are connected in parallel.

4. The support for fluorescence polarization immunoassay according to claim 1, wherein the fluorescent dye is one or more selected from a group consisting of fluorescein, dansyl, pyrene, rhodamine, dialkylaminonaphthalene, dialkylaminonaphthalenesulfonyl, indolenine, and ruthenium.

5. The support for fluorescence polarization immunoassay according to claim 1, wherein the fluorescent dye has a fluorescence life of 1 to 3,000 nanoseconds.

6. A fluorescence polarization immunoassay kit comprising:
the support for fluorescence polarization immunoassay according to claim 1; and
a solvent for dissolving the target substance.

7. A method for fluorescence polarization immunoassay, the method comprising:
adding a sample solution containing the target substance to the recesses of the support for fluorescence polarization immunoassay according to claim 1;
causing the target substance, the antibody, and the fluorescent labeling substance to react in the recesses; and
performing a fluorescence polarization immunoassay of the recesses at a temperature of 4 to 40° C.

8. A support for fluorescence polarization immunoassay of a target substance in a sample, the support comprising:
multiple recesses, the recesses being loaded with an antibody having a binding ability to the target substance and a fluorescent labeling substance in which the target substance is labeled with a fluorescent dye,
wherein the support comprises a plurality of types of the recesses resulting from difference in a binding affinity of the antibody for the target substance,
wherein the support comprises multiple groups each including multiple homogeneous recesses, the multiple homogeneous recesses being loaded with a same substance and having a same loaded amount, and
wherein the antibody and the fluorescent labeling substance are bound to a surface of the recesses in a way that, when a sample solution containing a the target substance is added to the recesses, the antibody and the fluorescent labeling substance can be released from the surface of the recesses into the sample solution.

9. The support for fluorescence polarization immunoassay according to claim 8, wherein the recesses are microfluidic channels.

10. The support for fluorescence polarization immunoassay according to claim 8, wherein some of the recesses are connected through a communication path and a branch path,
wherein the branch path connects some of the recesses with the communication path, and
wherein some of the recesses are connected in parallel.

11. The support for fluorescence polarization immunoassay according to claim 8, wherein the fluorescent dye is one or more selected from a group consisting of fluorescein, dansyl, pyrene, rhodamine, dialkylaminonaphthalene, dialkylaminonaphthalenesulfonyl, indolenine, and ruthenium.

12. The support for fluorescence polarization immunoassay according to claim 8, wherein the fluorescent dye has a fluorescence life of 1 to 3,000 nanoseconds.

13. A fluorescence polarization immunoassay kit comprising:
the support for fluorescence polarization immunoassay according to claim 8; and
a solvent for dissolving the target substance.

14. A support for fluorescence polarization immunoassay of a target substance in a sample, the support comprising:
multiple recesses, the recesses being loaded with an antibody having a binding ability to the target substance and a fluorescent labeling substance in which the target substance is labeled with a fluorescent dye,
wherein at least one of the multiple recesses is further loaded with a pH adjuster, and the support comprises a plurality of types of the recesses resulting from the presence or absence of the pH adjuster and/or differences in the type of the pH adjuster,
wherein the support comprises multiple groups each including multiple homogeneous recesses, the multiple homogeneous recesses being loaded with a same substance and having a same loaded amount, and
wherein the antibody and the fluorescent labeling substance are bound to a surface of the recesses in a way that, when a sample solution containing the target substance is added to the recesses, the antibody and the fluorescent labeling substance can be released from the surface of the recesses into the sample solution.

15. The support for fluorescence polarization immunoassay according to claim 14, wherein the recesses are microfluidic channels.

16. The support for fluorescence polarization immunoassay according to claim 14, wherein some of the recesses are connected through a communication path and a branch path,
wherein the branch path connects some of the recesses with the communication path, and
wherein some of the recesses are connected in parallel.

17. The support for fluorescence polarization immunoassay according to claim 14, wherein the fluorescent dye is one or more selected from a group consisting of fluorescein, dansyl, pyrene, rhodamine, dialkylaminonaphthalene, dialkylaminonaphthalenesulfonyl, indolenine, and ruthenium.

18. The support for fluorescence polarization immunoassay according to claim 14, wherein the fluorescent dye has a fluorescence life of 1 to 3,000 nanoseconds.

19. A fluorescence polarization immunoassay kit comprising:
the support for fluorescence polarization immunoassay according to claim 14; and
a solvent for dissolving the target substance.

* * * * *